US007867476B2

(12) United States Patent
Knowlton et al.

(10) Patent No.: US 7,867,476 B2
(45) Date of Patent: Jan. 11, 2011

(54) METHOD AND MATERIALS FOR USE IN DIAGNOSING VIRAL MYOCARDITIS

(75) Inventors: Kirk Knowlton, Escondido, CA (US); Sotirios Tsimikas, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 754 days.

(21) Appl. No.: 10/591,092

(22) PCT Filed: Mar. 24, 2005

(86) PCT No.: PCT/US2005/010078

§ 371 (c)(1),
(2), (4) Date: Jul. 12, 2007

(87) PCT Pub. No.: WO2005/091750

PCT Pub. Date: Oct. 6, 2005

(65) Prior Publication Data

US 2007/0292345 A1    Dec. 20, 2007

Related U.S. Application Data

(60) Provisional application No. 60/556,154, filed on Mar. 24, 2004.

(51) Int. Cl.
*A61K 49/00* (2006.01)
(52) U.S. Cl. ............... 424/9.1; 424/1.11; 424/1.49; 424/9.2; 435/5
(58) Field of Classification Search ........... 424/1.11, 424/1.49, 1.65, 1.69, 1.81, 1.85, 1.89, 9.1, 424/9.2, 9.3, 9.4, 9.5, 9.6, 9.7, 9.8, 194.1, 424/130.1, 133.1, 135.1, 136.1, 139.1, 141.1, 424/146.1, 159.1, 178.1, 184.1, 193.1, 809; 435/5
See application file for complete search history.

(56) References Cited

U.S. PATENT DOCUMENTS

| 5,308,752 | A | * | 5/1994 | Campbell et al. .......... 435/7.21 |
| 5,418,139 | A | | 5/1995 | Campbell |
| 5,571,698 | A | | 11/1996 | Ladner et al. |
| 6,057,098 | A | | 5/2000 | Buechler et al. |

FOREIGN PATENT DOCUMENTS

| DE | 3939200 | 5/1991 |
| DE | 19846271 | 4/2000 |
| FR | 2851046 | 8/2004 |
| WO | WO 89/09790 | 10/1989 |

OTHER PUBLICATIONS

Badorff et al, Nature Medicine, Mar. 1999, vol. 5, No. 3, pp. 320-326.*
Cabily, et al. "Generation of Antibody Activity from Immunoglobulin Polypeptide Chains Produced in *Escherichia coli*", *Proc. Natl. Acad. Sci.* USA, 81:3273, 1984.
Cwirla et al., "Peptides on Phage: A vast library of peptides for identifying ligands", Proc. Natl. Acad. Sci. USA 87, 6378-82, 1990.
Devlin et al., "Random Peptide Libraries: A Source of Specific Protein Binding Molecules", Science 249, 404-6, 1990.
Feldman and McNamara, "Myocarditis", *New Engl.J.Med.*, 343:1388-1398, at 1393 (2000).
Fujiwara et al., "Synthesis of Human C-Type Natriuretic Peptide 22 Using Chlorotrityl Resin and Tetrafluoroboric Acid Deprotection", Chem. Pharm. Bull. (Tokyo) 44: 1326-31, 1996.
Huse, et al., "Generation of a Large Combinatorial Library of the Immunoglobulin Repertoire in Phage Lambda", *Science*, 246:1275-1281, 1989.
Huse et al., "Application of a Filamentous Phage pVIII Fusion Protein system Suitable for Efficient Production, Screening, and Mutagenesis of F(ab) Antibody Fragments", J. Immunol. 149, 3914-3920 (1992.
Ishiwata, et al., "Studies of 18F-labeled pyrimidines", *Eur.J.Nucl. Med.*, 9:185-189, 1984.
Keough, et al, "An Improved Method For Synthesis and Purification of 125I or 131I labeled Carrier-Free 5-IODO-1'-Deoxyuridine", *J.Labeled Compound Radiopharm.*, 14:83-90, 1978.
Kiso et al., "Solution-Phase Synthesis of Porcine Brain Natriuretic Peptide (pBNP) Using S-Trimethylacetamido-methylcystein", Chem. Pharm. Bull. (Tokyo) 38: 1192-99, 1990.
Kubota, et al., "Differential Diagnosis of AH109A Tumor and Inflammation by Radioscintigraphy with L-[Methyl-11C] methionine", *Jpn.J.Cancer Res.*, 80:778-782, 1989.
Makrigiorgos, et al., "Inhomogeneous Deposition of Radiopharmaceuticals at the Cellular Level: Experimental Evidence and Dosimetric Implications", *J.Nucl.Med.*, 31:1358-1363, 1990.

(Continued)

*Primary Examiner*—D L Jones
(74) *Attorney, Agent, or Firm*—DLA Piper LLP (US)

(57) ABSTRACT

The invention consists of assay methods, assay kits and antibodies for detecting the polypeptide fragments of dystrophin protein cleavage by enteroviral protease 2A as a result of an enteroviral infection in the heart. The presence of dystrophin cleavage products in the myocytes or blood of a subject is diagnostic for enteroviral infection and myocarditis resulting therefrom.

6 Claims, No Drawings

OTHER PUBLICATIONS

Mostafavi et al, Synthesis, Purification and Biological Activity of (SER10-Phosphatidyl)-Urodilatin (Phosphourodilatin), Biomed. Pept. Proteins Nucleic Acids 1: 255-60, 1995.

Mullinax, et al., "Identification of human antibody fragment clones specific for tetanus toxoid in a bacteriophage λ immunoexpression library", *Proc. Natl. Acad. Sci.*, 87:8095-8099, 1990.

Riechmann, et al., "Reshaping Human Antibodies for Therapy", *Nature* 332:323, 1988.

Scott and Smith, "Searching for Peptide Ligands with an Epitope Library", Science 249, 386-88, 1990.

Shaw, et al.,"Characterization of a Mouse/Human Chimeric Monoclonal Antibody (17-1A) to a Colon Cancer Tumor-Associated Antigen", *J. Immun.*, 138:4534 (1987.

Sheng, et al.,"Cardiotrophin 1 (CT-1) Inhibition of Cardiac Myocyte Apoptosis Via A Mitogen=activated Protein Kinase-dependent Pathway", *J.Biol.Chem.*, 272:5783-5791 (1997.

Spira, et al., "The Identification of Monoclonal Class Switch Variants by Sib Selection and an ELISA Assay", *J. Immunol. Methods*, 74:307, 1984.

Sun, L.K., et al., "Chimeric Antibody With Human Constant Regions and Mouse Variable Regions Directed Against Carcinoma-Associated Antigen 17-1A", *Proc. Natl. Acad. Sci.* USA, 84:214-218 (1987).

Steplewski, et al.,"Isolation and Characterization of Anti-monosialoganglioside Monoclonal Antibody 19-9 Class-Switch Variants", *Proc. Natl. Acad. Sci.* U.S.A., 82:8653, 1985.

Ward et al., "Binding Activities of a Repertoire of Single Immunoglobulin Variable Domains Secreted from *Escherichia coli*", (1989) *Nature* 341:544-546).

Wilson et al., "Simplified Conjugation Chemistry for Coupling Peptides to F(ab') Fragments: Autologous Red Cell Agglutination Assay for HIV-1 Antibodies", (1994) J. Immunol. Methods 175:267-273.

Yarmush M.L, et al., "Coupling of Antibody-Binding Fragments to Solid-Phase Supports: Site-Directed Binding of F(ab')2 Fragments", (1992) J. Biochem. Biophys. Methods 25:85-97.

Miyatake et al, "Dystrophin: localization and presumed function," Muscle & Nerve, 14(2): 113-119 (1991).

Chevron et al, "Expression and subcellular localization of dystrophin in skeletal, cardiac and smooth muscles during the human development," Neurmuscular Disorders, 4( 5-6):419-432 (1994).

Lee et al, "Dissociation of sarcoglycans and the dystrophin carboxyl terminus from the sarcolemma in enteroviral cardiomyopathy," Circulation Research, 87(6): 489-495 (2000).

Supplemental European Search Report from Corresponding European Patent Application No. 05741824.

* cited by examiner

METHOD AND MATERIALS FOR USE IN DIAGNOSING VIRAL MYOCARDITIS

CROSS REFERENCE TO RELATED APPLICATION

This patent application is the national stage entry of PCT/US05/10078 filed on Mar. 24, 2005, which claims priority from U.S. Provisional Application 60/556,154 filed on Mar. 24, 2004.

STATEMENT OF GOVERNMENT SUPPORT

Support for work related to this invention was provided by the National Institute of Health under Grant No. RO1 HL57365-01. The Government may have certain rights in the invention.

BACKGROUND OF THE INVENTION

Heart failure is a leading cause of cardiovascular mortality in the US and Europe and is a 'hallmark' of dilated cardiomyopathy, a multifactorial disease in which there is evidence of enteroviral infection in up to 30% of cardiomyopathy patients. Despite the relative prevalence of these infections, however, diagnosis remains extremely difficult. At present, enteroviral infections of the heart may only be confirmed by biopsy, but even the assay used on biopsy samples is neither sensitive nor specific.

In cardiac muscle, the dystrophin-glycoprotein complex includes dystrophin and the dystrophin-associated glycoprotein, β-sarcoglycan, β-dystroglycan; and the recently described sarcospan. This complex is part of the extrasarcomeric cytoskeleton that collectively connects the internal F-actin-based cytoskeleton to laminin-2 of the extracellular space. Thereby, it is thought to play an important role in the transmission of mechanical force to the extracellular matrix.

Genetic defects in these proteins are the cause of human limb-girdle muscular dystrophy type 2D, 2E, 2C, and 2F, and can caused dilated cardiomyopathy in humans. Mutations in dystrophin also cause Duchenne and Becker muscular dystrophy, both of which have a high incidence of dilated cardiomyopathy. In addition, dystrophin mutations are a cause of X-linked dilated cardiomyopathy. These studies and others have led to the paradigm that familial dilated cardiomyopathy can result from defective transmission of mechanical force from the sarcomere to the extracellular matrix and that disruption of the dystrophin-glycoprotein complex may be a common mechanism that causes cardiomyopathy.

Although the importance of genetic defects of the dystrophin-glycoprotein complex in hereditary cardiomyopathy is well established, little is known about its role in acquired cardiomyopathy. A subset of human acquired dilated cardiomyopathy is associated with an enteroviral infection of the heart, in particular, coxsackie B viruses. Coxsackie B viruses are members of the picorniaviridae family, enterovirus genus.

The inventors' work has indicated that enteroviral protease 2A cleavage of dystrophin plays a role in the molecular pathogenesis of enterovirus-induced cardiomyopathy. However, the mechanisms by which enterovirus infection can cause cardiomyopathy are not clear, and no diagnostic test directed to cleavage products of dystrophin in the heart that would allow for early treatment or prognosis is available.

SUMMARY OF THE INVENTION

The invention provides a highly sensitive and specific diagnostic method to determine whether a patient's heart has been infected with a picornavirus such as coxsackievirus, or enterovirus. The method can be applied either in vitro or in vivo; e.g., as a simple blood test, or through myocardial imaging. In contrast, existing methods for diagnosis of myocardial viral infection require that heart tissue be biopsied for laboratory analysis and, even then, the test is of "limited sensitivity and specificity" (Feldman and McNamara, New Engl. J Med., 343:1388-1398, at 1393 (2000)). The invention therefore provides a significant improvement in diagnostic techniques for virus mediated acquired cardiomyopathy.

Thus, in one embodiment of the invention, a method is provided for detecting an enteroviral infection in a subject's heart, the method comprising in vivo imaging of myocytes for the presence of a dystrophin cleavage product therein, wherein the presence of the cleavage product is a marker for enteroviral-mediated cleavage of dystrophin. Detection of such dystrophin cleavage products is performed according to the invention by administering a diagnostically effective amount of detectably labeled dystrophin fragment antibody into the subject's cardiovascular circulation or tissue, wherein binding of the antibody indicates that a dystrophin cleavage product resulting from an enteroviral infection is present in one or more of the myocytes.

In a further embodiment of the invention, a method is provided for detecting an enteroviral infection in a subject's heart, the method comprising in vitro immunological detection of a dystrophin cleavage product in blood or cardiovascular tissue obtained from the subject, wherein the presence of the cleavage product is a marker for enteroviral-mediated cleavage of dystrophin. Detection of such dystrophin cleavage products is performed according to the invention in an assay using a detectably labeled dystrophin fragment antibody, wherein binding of the antibody indicates that a dystrophin cleavage product resulting from an enteroviral infection is present in the blood or cardiovascular tissue assayed.

DETAILED DESCRIPTION OF THE PREFERRED EMBODIMENTS

I. Cleavage of Dystrophin Protein and Relationship to Myocarditis.

Dystrophin, a component of the dystrophin-glycorprotein complexes, is a 427-kDa protein with four main domains: an N-terminal domain, a spectrin-like repeat rod domain, a cysteine-rich domain, and a C-terminal domain (FIG. 1). The N-terminal domain as well as an epitope in the rod domain bind actin, whereas the cysteine-rich domain and C terminus contribute to binding of dystroglycan. In the rod domain of dystrophin, four hinge segments (H1-H4) have been identified that are accessible to proteolytic cleavage. The protease 2A cleavage site at residue 2,434 lies within the H3 region between repeats 19 and 20, and produces a fragment of between 280 and 300 kDA molecular weight (from the human protein, a 282 kDA fragment) (the "2434 cleavage product"). Additional cleavage at residue 588 produces a shorter fragment of between 210-230 kDa (from the human protein, a 214 kDa fragment) (the "588 cleavage product").

Although the invention is not limited by any theory as to the particular mechanism of pathogenesis involved in enteroviral infection of the heart, it is believed that cleavage by protease 2A in the region of residue 2434 of dystrophin would lead to abnormalities in myocyte function similar to those in Duchenne muscular dystrophy where there are frame-shift mutations in this region of dystrophin.

Enteroviruses are typically released from the cell by disruption of the cell membrane. Lack of dystrophin weakens the cytoskeleton and increases cell membrane permeability, as has been shown in mdx mice and mice that lack both dystrophin and utrophin. Thus, Coxsackievirus may facilitate its propagation through proteolyis of host cell structural molecules such as dystrophin, thereby enhancing viral spread in the heart and contribute to the pathogenesis of viral heart disease. It may also be important for allowing antibodies to access the cytosol of the myocyte and for escape of dystrophin cleavage products into the blood.

The invention is based on the discovery and premise that cleavage of dystrophin produces a new conformation at the cleavage site that can be exploited for identification by a protease 2A-specific dystrophin cleavage antibody.

II. Antibody Specific for Dystrophin Cleavage Fragments.

The invention provides means for detecting enteroviral protease 2A cleavage products of dystrophin in the cytosol of infected myocytes. The appearance of such cleavage products is indicative of the presence of an enteroviral infection of the heart, and possible onset of acquired cardiomyopathy. Cleavage products may be detected according to the invention within 12 hours of infection. Thereafter, weakening of infected cell membranes permits the cleavage products to enter the bloodstream. Thus, in the assay of the invention, protease 2A cleavage products of dystrophin are detectable through imaging of the heart in vivo as soon as 12 hours following an infection, and/or in serum in vitro at times thereafter.

To these ends, antibodies and/or Fab fragments (hereafter, collectively, "dystrophin epitope-specific antibodies") made according to the invention are specific for an enteroviral protease 2A cleavage product of dystrophin (hereafter, a "dystrophin cleavage product"). The specificity of the dystrophin epitope-specific antibodies for these cleavage products results from alterations to the conformation of the dystrophin cleavage site at amino acids recognized by protease 2A, and enables their use in highly sensitive assays indicative of the presence of an enteroviral infection in the host; e.g., in the host myocardium.

The 2434 and 588 residues of dystrophin are both located within the protein's rod domain. Dystrophin epitope-specific antibodies which are highly specific for either one of the 2434 or 588 cleavage products, but not both, are preferred for use in the invention. Dystrophin epitope-specific antibodies with specificity for the 2434 cleavage product are especially preferred for use in the invention.

Residue 2434 lies within a hinge segment (H3) of dystrophin, while residue 588 lies outside of the hinge segment regions. Dystrophin epitope-specific antibodies specific to regions of the rod domain of dystrophin encompassing a hinge segment can be expected to be more highly specific for the 2434 cleavage product than antibodies generated to regions of the rod domain lacking a hinge segment.

Dystrophin epitope-specific antibodies useful in the invention (preferably monoclonal antibodies) may be generated according to techniques which are well known in the art, and need not be described in detail here. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

The generation and selection of antibodies may be accomplished several ways. For example, one way is to purify polypeptides of interest or to synthesize the polypeptides of interest using, e.g., solid phase peptide synthesis methods well known in the art. See, e.g., Guide to Protein Purification, Murray P. Deutcher, ed., Meth. Enzymol. Vol 182 (1990); Solid Phase Peptide Synthesis, Greg B. Fields ed., Meth. Enzymol. Vol 289 (1997); Kiso et al., Chem. Pharm. Bull. (Tokyo) 38:1192-99, 1990; Mostafavi et al., Biomed. Pept. Proteins Nucleic Acids 1: 255-60, 1995; Fujiwara et al., Chem. Pharm. Bull. (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. For example, a method for the identification and isolation of an antibody binding domain which exhibits binding with a peptide of the invention is the bacteriophage λ vector system. This vector system has been used to express a combinatorial library of Fab fragments from the mouse antibody repertoire in *Escherichia coli* (Huse, et al., *Science,* 246:1275-1281, 1989) and from the human antibody repertoire (Mullinax, et al, *Proc. Natl. Acad. Sci.,* 87:8095-8099, 1990).

Antibodies exhibiting binding for a preselected ligand may be identified and isolated from these antibody expression libraries. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies, including their binding fragments, and screening and selecting for affinity and specificity for the various polypeptides, but these approaches do not change the scope of the invention. In addition, methods of producing chimeric antibody molecules with various combinations of "humanized" antibodies are known in the art and include combining murine variable regions with human constant regions (Cabily, et al. *Proc. Natl. Acad. Sci. USA,* 81:3273, 1984), or by grafting the murine-antibody complementary determining regions (CDRs) onto the human framework (Rieclunalm, et al., Nature 332:323, 1988). This invention therefore further provides chimeric dystrophin epitope-specific antibodies. Chimeric antibodies are constructed by recombinant DNA technology, and are described in, for example, Shaw, et al., *J. Immun.,* 138:4534 (1987), Sun, L. K., et al, *Proc. Natl. Acad. Sci. USA,* 84:214-218 (1987).

Under certain circumstances, monoclonal antibodies of one isotype might be more preferable than those of another in terms of their diagnostic or therapeutic efficacy. Particular isotypes of a monoclonal antibody can be prepared secondarily, from a parental hybridoma secreting monoclonal antibody of different isotype, by using the sib selection technique to isolate class-switch variants (Steplewski, et al., *Proc. Natl. Acad. Sci. U.S.A.,* 82:8653, 1985; Spira, et al, *J. Immunol. Methods,* 74:307, 1984). Thus, the invention includes class-switch variants of dystrophin epitope-specific antibodies having binding specificity comparable to that of any of the dystrophin epitope-specific antibodies described herein.

It is also possible to determine, without undue experimentation, if a monoclonal antibody has the same specificity as a dystrophin epitope-specific antibody described herein by, for example, ascertaining whether the former prevents the latter from binding to a target dystrophin fragment. If the monoclonal antibody being tested competes for binding with the dystrophin epitope-specific antibody (as shown by a decrease in binding by the monoclonal antibody of the invention), then the two monoclonal antibodies bind to the same, or a closely related, epitope.

An anti-idiotypic antibody can be prepared by immunizing an animal with a dystrophin epitope-specific antibody. The immunized animal will recognize and respond to the idiotypic determinants of the immunizing antibody and produce an antibody to these idiotypic determinants. By using the anti-idiotypic antibodies of the immunized animal, it is now possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

For in vivo administration, dystrophin epitope-specific antibodies will preferably be formulated in a pharmaceutically acceptable carrier, most preferably a liquid (see, standard reference Remington's Pharmaceutical Sciences, which is incorporated herein by reference to illustrate knowledge in the art concerning suitable pharmaceutical carriers). Exemplary liquid carriers are saline, Ringer's solution, syrup, peanut oil, olive oil and like emulsions. The formulation can be in the form of an aqueous or nonaqueous liquid suspension and may include pharmaceutically acceptable preservatives.

For use in vivo or in vitro, dystrophin epitope-specific antibodies can also be bound to many different carriers for use in numerous immunoassay formats known to those of ordinary skill in the art (e.g., lateral flow or radioimmunoassay). Examples of suitable carriers include, for in vivo use, proteins (e.g., BSA and lysine) and, for in vitro use, glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

III. Diagnostic Use of Dystrophin Epitope-Specific Antibodies.

A. Methods for Performing in vivo Assays for Dystrophin Cleavage Products in Blood or Tissue Samples.

According to this embodiment of the invention, a dystrophin epitope-specific antibody is given to a host in a dose which is diagnostically effective. The term "diagnostically effective" means that the amount of dystrophin epitope-specific antibody is administered in sufficient quantity to enable detection of dystrophin cleavage products in host myocytes or blood.

Imaging post-injection is preferably made immediately following to about 24 hours after injection of the antibody, depending on the half-life of the radiolabel used and condition of the patient. Increased binding of detectably labeled antibody relative to a control (e.g., data evidencing the binding characteristics of the antibody to normal tissue) is indicative of the presence of enteroviral infection in host cardiovascular tissue.

As a rule, the dosage of detectably labeled dystrophin epitope-specific antibody for in vivo diagnosis will vary depending on such factors as age, sex, and extent of disease of the individual. The dosage of dystrophin epitope-specific antibody can vary from about 0.01 mg/m$^2$ to about 500 mg/m$^2$, preferably 0.1 mg/m$^2$ to about 200 mg/m$^2$, most preferably about 0.1 mg/in² to about 10 mg/m². Such dosages may vary, for example, depending on whether multiple injections are given, tissue, and other factors known to those of skill in the art.

The dosage of radioisotope label required to detect enteroviral infection in a host will also vary with the radioactivity of the radioisotope and will be taken into account in determining a suitable dose to be given of an imaging antibody according to the invention. For example, the mean lethal dosages of both $^{125}$I and $^{123}$I have been calculated at about 79+/−9 cGy (in Chinese hamster ovary cells; see, e.g., Makrigiorgos, et al., *Radiat. Res.*, 118:532-544). For diagnostic purposes, the dosage will be less than the mean lethal dose for the radioisotope.

For example, with respect to the half-life of common radioisotopes, the half-life of $^{123}$I at a dose between 1 and 20 microCi (mCi) is about 13 hours, while the half-life of $^{131}$I at a dose of less than 5 mCi is about 8 days. With respect to positron emitters, the half-life of $^{11}$C at a dose of 200 mCi or more is only 20 minutes, while the half-life of $^{18}$F at a dose of only 50 mCi is nearly six times as long. For example, it is expected that a useful dose of $^{123}$I-labeled antibody would be between 1 and 20 mCi, while less than 5 mCi of the longer-lived $^{131}$I would be used (e.g. 0.5-5 mCi) and approximately 200 mCi $^{11}$C can be used (e.g., 100-300 mCi). Thus, for use according to the invention, the preferred dose of agents including radioisotopes with longer half-lives will be less than the preferred dose of agents including radioisotopes with shorter half-lives.

One of ordinary skill in nuclear medicine would now to take the above and other salient characteristics of the radioisotopes into account when calculating an appropriate dosage. As a general matter, it is expected that a useful dose of detectably labeled dystrophin epitope-specific antibody would deliver between about 0.5 and about 500 millicuries (mCi). In general, this dosage range will not vary substantially with the weight, age and sex of the host. However, in juvenile hosts, dosages in the lower spectrum of each preferred dosage range will be preferred, in order to limit accumulation of radioactivity in dividing cells.

Selection and modification of particular doses for each detectably labeled dystrophin epitope-specific antibody to be used in the invention is within the ordinary level of skill in the art. In particular, dosimetry calculations are well-known in the art which permit estimation of the distribution and radioactive burden to host tissues and cells on administration of radioisotopes. For review in this regard, those of skill in the art may wish to consult Makrigiorgos, et al., *J. Nucl. Med.*, 31:1358-1363, 1990, the disclosure of which is incorporated herein by this reference to illustrate knowledge in the art concerning dosimetric calculations of radioactivity distribution.

The detectably labeled dystrophin epitope-specific antibodies of the invention will be administered by a parenteral route selected to best target the suspected site of plaque formation; i.e., intravascular or intra-arterial injection. Antigen administered to enhance clearance of residual radioactivity in background (blood) will be administered by the same routes utilized to administer the antibody.

For monitoring the course of infection in a host as well as the host's responsiveness to therapy, the heart may be imaged according to the invention more than once. Clearance of any previously administered radioactive agents (including those of the invention and chemotherapeutic agents) should be considered to limit detection of residual radioactivity. Rates of clearance may be determined based on known clearance rates for the particular radioisotopes present, or may be inferred by reimaging the host prior to readministering a detectably labeled dystrophin epitope-specific antibody according to the invention. Accumulation of the detectably labeled dystrophin epitope-specific antibodies of the invention in background will also be taken into account in this regard to maximize the target-to-background radioactivity ratios achieved in each imaging session.

Protocols and formulas for use in determining target-to-background ratios for radioactivity are well-known in the art. Depending on the radioisotope present, the detectably labeled dystrophin epitope-specific antibody may accumulate to some degree in tissues adjacent or distant from target tissues. Nonspecific binding of the detectably labeled dystrophin epitope-specific antibodies of the invention is minimized by the high binding specificity of the antibodies for dystrophin cleavage products in enteroviral infection.

B. Labeling of Dystrophin Epitope-Specific Antibodies for in vivo Imaging of Infected Myocytes.

In vivo diagnostic imaging according to the invention is performed using dystrophin dystrophin epitope-specific antibodies as described above which have been detectably labeled; i.e., joined to a radioisotope whose presence in the body may be identified using a detection instrument. Those of ordinary skill in the art will be familiar with, or can readily ascertain the identity of, techniques and instruments for in vivo detection of radioactivity provided in the host by detachably labeled dystrophin epitope-specific antibodies used according to the invention.

To detect radioactivity provided by gamma emitter detectably labeled dystrophin epitope-specific antibodies, an instrument commonly known as a gamma camera (i.e., a system of scintillation crystals or photo multiplier tubes for analysis of radioactive decay) will be used to detect gamma emission from the detectably labeled dystrophin epitope-specific antibody. To detect radioactivity provided by positron emitter detectably labeled dystrophin epitope-specific antibodies, techniques and instruments for positron emission tomography (PET) and single photon positron emission spectography (SPECT) are available to, and well-known in, the art. Those of ordinary skill in the art will also recognize that the dystrophin epitope-specific antibodies of the invention may be coupled to paramagnetic isotopes for use in magnetic resonance imaging (MRI), may be coupled to paramagnetic isotopes for use in electron spin resonance (ESR) or may be covalently attached to contrast media for use in ultrasound. In general, any conventional method for visualizing diagnostic imaging can be utilized.

The selection of a detectably labeled dystrophin epitope-specific antibody and detection technique suitable for a given application is within the ordinary level of skill in the art. Factors to be considered in this respect include the existence of any host sensitivity to a particular radioisotope, in vivo toxicity and efficiency of such molecules, potential pharmaceutical interactions between the detectably labeled dystrophin epitope-specific antibody and other medications taken by the host, the availability of particular detection instruments, and cost of materials.

Thus, for in vivo diagnostic imaging, the type of detection instrument available is a major factor in selecting a given labeling agent. For radioactive labeling agents, the radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylene triaminepentacetic acid (DTPA) and ethylenediaminetetraacetic acid (EDTA) and similar molecules. Typical examples of radioisotopes which can be bound to the dystrophin epitope-specific antibodies of the invention are $^{111}$In, $^{97}$Ru, $^{67}$Ga, $^{68}$Ga, $^{72}$As, $^{89}$Zr, $^{90}$Y, $^{201}$Tl, $^{157}$Gd, $^{55}$Mn, $^{162}$Dy, $^{52}$Cr, $^{56}$Fe, $^{122}$I, $^{123}$I, $^{124}$I, $^{125}$I, $^{126}$I, $^{131}$I, $^{80}$Br, $^{82}$Br, $^{75}$Br, $^{76}$Br, $^{77}$Br, $^{90}$Br, $^{18}$Fl, $^{11}$C, $^{13}$N and $^{99m}$-technetium. Particularly preferred for their safety and relative ease of use and detection are $^{111}$In and $^{99m}$technetium.

Those of ordinary skill in the art will be familiar with, or can readily ascertain, synthesis methods appropriate to the preparation of radioisotopically labeled dystrophin epitope-specific antibodies for use in the inventive method. For example, other suitable radioiodination labeling techniques are taught in Keough, et al, *J. Labeled Compound Radiopharm.*, 14:83-90, 1978. In addition, techniques useful in labeling molecules with positron emitters (e.g., $^{18}$fluorine) are known in the art and include the technique disclosed in Ishiwata, et al., *Eur. J. Nucl. Med.*, 9:185-189, 1984 ($^{18}$fluorine labeling of deoxyuridine). Techniques for labeling with non-halogen radioisotopes (such as $^{11}$C) are also well-known and include the technique referred to in Kubota, et al., *Jpn. J. Cancer Res.*, 80:778-782, 1989.

C. Methods for in vitro Use of the Dystrophin Epitope-Specific Antibodies to Bind Dystrophin Cleavage Products in Biological Samples.

The dystrophin epitope-specific antibodies are especially useful in vitro for purposes of diagnosis, preferably using a simple blood draw. Conveniently, the antibodies are evaluated for dystrophin cleavage product binding by immunoassay performed on a biological sample of plasma, coronary tissue or vascular tissue obtained from a host.

An especially useful in vitro assay for detection of dystrophin cleavage products in a serum or tissue sample is an ELISA or other well-known immunoassay technique suitable for use with either fluid or solid biological samples. An example of an immunoassay suitable for this purpose (i.e., an immunoblot method) is described further in Example 1 below. However, those skilled in the immunological arts will recognize that dystrophin cleavage products may be detected using the antibodies described above in other immunoassay formats, in either liquid or solid phase (when bound to a carrier).

Detection of dystrophin cleavage products using the dystrophin epitope-specific antibodies described can be done utilizing immunoassays which are run in either the forward, reverse, or simultaneous modes, including immunohistochemical assays on physiological samples. Suitable immunoassay protocols include competitive and non-competitive protocols performed in either a direct or indirect format. Examples of such immunoassays are the radioimmunoassay (RIA) and the sandwich (immunometric) assay. Those of skill in the art will know, or can readily discern, other immunoassay formats without undue experimentation.

D. Labels for in vitro Assay Use.

In addition, the dystrophin epitope-specific antibodies utilized in the immunoassays may be detectably labelled. For example, suitable labels include radioisotopes, an enzyme substrate or inhibitor, an enzyme, a radiopaque substance (including colloidal metals), a fluorescor, a chemiluminescent molecule, bioluminescent compounds, colloidal metals, liposomes containing any of the above labels, or a specific binding pair member.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

Suitable radioisotopes for in vitro use include $^3$H, $^{125}$I, $^{133}$I, $^{32}$P, $^{42}$C, and $^{35}$S. Dystrophin cleavage products labeled by means of a radioisotope may be detected directly by gamma counter or by densitometry of autoradiographs, by Southern blotting of the amplified fragments combined with densitometry. Examples of radiopaque substances for use in radio-immunoassays are colloidal gold or magnetic particles.

Examples of suitable chemiluminescent molecules for use in chemiluminescent assays are acridines or luminol. Examples of suitable fluorescers for use in fluorescence assays are fluorescein, phycobiliprotein, rare earth chelates, dansyl or rhodamine. Further, examples of suitable enzyme substrates or inhibitors for use in ELISA and other enzyme mediated assays are compounds which will specifically bind to horseradish peroxidase, glucose oxidase, glucose-6-phosphate dehydrogenase, beta-galactosidase, pyruvate kinase or alkaline phosphatase acetylcholinesterase.

Those of ordinary skill in the art will know of other suitable labels for binding to the dystrophin epitope-specific antibodies of the invention, or will be able to ascertain such, using routine experimentation. Furthermore, the binding of these labels to the dystrophin epitope-specific antibodies of the invention can be done using standard techniques common to those of ordinary skill in the art.

E. Assay Kits.

Dystrophin cleavage products detection kits may be prepared for use in laboratory and clinical settings which include reagents useful in the methods described above. For example, such a kit may include any or all of the following: detectably labelled dystrophin epitope-specific antibodies, dystrophin antigens, control antibodies, and reagant coated microtiter plates, or an array; e.g., microarray chips suitable for use in biological assays.

Examples illustrating practice of the method of the invention are set forth below. These examples should not, however, be considered to limit the scope of the invention, which is defined by the appended claims. In the examples, abbreviations, if used, have the following meanings: "min." refers to minutes, "hrs" and "h" refer to hours, "d" refers to days, "wk" refers to weeks, "iv" refers to intravenous, "mAb" refers to monoclonal antibody, and measurement units (such as "ml") are referred to by standard abbreviations.

EXAMPLES

Example 1

In Vitro Detection of Dystrophin Cleavage Products Following Virus Infection

To detect dystrophin cleavage products in Coxsackievirus B3 infected cardiac myocytes in vitro, neonatal rat ventricular myocytes were cultured with Coxsackievirus B3. Rat neonatal myocytes, an established myocyte culture model (Sheng, et al, *J. Biol. Chem.*, 272:5783-5791 (1997), incorporated herein by reference to illustrate an animal model useful in the invention), are known to express dystrophin and can be infected with Coxsackievirus B3. Protein extracts were isolated after infection and analyzed for the presence of dystrophin rod domain-containing fragments by western blot with the Dy4/6D3 antibody against the intact dystrophin rod domain There was a substantial decrease in the intensity of the full-length dystrophin to very low levels by 36 hours after infection, while dystrophin cleavage products were evident beginning at 12 hours after infection, before the generalized cytopathic effect appeared. The cleavage products were the same size as those seen after recombinant purified protease 2A was added to myocyte extracts. In contrast, dystrophin was not cleaved after infection with wild-type adenovirus 5 at a time point associated with a considerable cytopathic effect.

Appearance of dystrophin cleavage products corresponds with cleavage of the known protease 2A-substrate eIF4G-1. Partial cleavage of eIF4G-1 was detectable as early as 8 hours after infection. As with dystrophin, cleavage of eIF4G-1 was specific to Coxsackievirus infection. Appearance of this known cleavage product is therefore a suitable control for use in assays performed according to the invention.

Example 2

Detection of Dystrophin Disruption Following Virus Infection In Vivo

To detect enterovirus-mediated cleavage of dystrophin in the intact heart, both immuno-competent and SCID mice were infected with Coxsackievirus B3. SCID mice lacking both T lymphocytes and B lymphocytes were used to differentiate effects secondary to the host immune response from direct effects of the virus on the cardiac myocyte.

Seven days after intraperitoneal injection of $1 \times 10^3$ PFU of Coxsackievirus B3, the hearts of both immunocompetent and SCID mice had evidence of dystrophin cleavage on in vivo examination. Cleavage is confirmed, according to the invention, thorugh in vivo or in vitro assaying with dystrophin epitope-specific antibodies.

The main dystrophin cleavage product was the 2434 cleavage product, which corresponded with the larger fragment seen after the addition of purified protease 2A to myocyte protein extracts in vitro. Unlike the complete cleavage of dystrophin that results from Coxsackievirus 83 infection of cultured myocytes, there was not a substantial decrease in full-length dystrophin, as Coxsackievirus B3 does not infect all myocytes in vivo.

The invention having been fully described, its scope, including equivalents apparent to those of ordinary skill in the art, is defined by the appended claims:

What is claimed is:

1. A method for detecting an enteroviral infection in a subject's heart, the method comprising in vitro immunological detection of a dystrophin cleavage product in blood or cardiovascular tissue obtained from the subject, wherein the dystrophin cleavage product is produced by enteroviral protease 2A cleavage of the rod domain of dystrophin, wherein the detection is performed in an immunoassay using a detectably labeled dystrophin epitope-specific antibody or Fab fragment thereof, wherein the dystrophin epitope-specific antibody or Fab fragment thereof is specific to the dystrophin cleavage product produced by enteroviral protease 2A cleavage of the rod domain of dystrophin, and wherein binding of the antibody indicates that a dystrophin cleavage product resulting from an enteroviral infection is present in the blood or cardiovascular tissue assayed.

2. The method according to claim 1, wherein the rod domain encompasses a hinge segment of dystrophin.

3. The method according to claim 1, wherein the dystrophin cleavage product is the 588 cleavage product.

4. The method according to claim 2, wherein the dystrophin cleavage product is the 2434 cleavage product.

5. The method according to claim 1, wherein the enteroviral infection is a Coxsackievirus infection.

6. The method according to claim 1, wherein the detection is performed on blood from the subject at least 12 hours following a suspected infection.

* * * * *